(12) United States Patent
Chase et al.

(10) Patent No.: US 7,322,952 B2
(45) Date of Patent: Jan. 29, 2008

(54) SUPPORT APPAREL SUCH AS BACK SUPPORT AND SYSTEM

(75) Inventors: David D. Chase, Albuquerque, NM (US); David G. Wilder, Iowa City, IA (US); Gary D. Shumate, Albuquerque, NM (US); Vijay K. Goel, Toledo, OH (US); Malcolm H. Pope, Scotland (GB)

(73) Assignee: University of Iowa Research Foundation, Iowa City, IA (US)

( * ) Notice: Subject to any disclaimer, the term of this patent is extended or adjusted under 35 U.S.C. 154(b) by 170 days.

(21) Appl. No.: 10/050,023

(22) Filed: Jan. 15, 2002

(65) Prior Publication Data

US 2003/0135134 A1 Jul. 17, 2003

(51) Int. Cl.
*A61F 5/00* (2006.01)
*A61B 5/103* (2006.01)
*A61B 5/117* (2006.01)

(52) U.S. Cl. .................. 602/19; 600/587; 600/594

(58) Field of Classification Search ............... 600/587, 600/594; 602/5, 19; 128/96.1, 99.1, 101.1
See application file for complete search history.

(56) References Cited

U.S. PATENT DOCUMENTS

| 2,552,475 | A | * | 5/1951 | Austlid | 602/19 |
| 4,884,562 | A | * | 12/1989 | Stone | 602/19 |
| 5,261,871 | A | * | 11/1993 | Greenfield | 602/26 |
| 5,548,843 | A | | 8/1996 | Chase et al. | 2/102 |
| 5,769,803 | A | * | 6/1998 | Brossard | 602/19 |
| 5,984,886 | A | * | 11/1999 | Miller | 602/19 |

OTHER PUBLICATIONS

Kong et al., "Prediction of Biomechanical Parameters in the Lumbar Spine During Static Sagittal Plane Lifting", Journal of Biomechanical Engineering, vol. 120, pp. 273-280 (Apr. 1998).
Kong et al., "Effects of Muscle Dysfunction on Lumbar Spine Mechanics", SPINE, vol. 21, No. 19, pp. 2197-2207 (1996).
Goel et al., "A Combined Finite Element and Optimization Investigation of Lumbar Spine Mechanics With and Without Muscles", SPINE, vol. 18, No. 11, pp. 1531-1541 (1993).
Udo et al., "The Effect of a Preventive Belt on the Incidence of Low-Back Pain (Part II): Investigation in Rice-Carrying Work", J. Science of Labour, vol. 68, No. 10 (1992).
Udo et al., "The Effect of a Preventive Belt on the Incidence of Low-Back Pain (Part III): Investigation in Crane Work", J. Science of Labour, vol. 69, No. 1 (1993).
Seonghee Lee, "Sudden Load and the Lower Back: Effect of Load Application and Lumbar Support", An Abstract of a thesis submitted in partial fulfillment of the requirement for the Doctor of Philosophy degree in Biomedical Engineering in the Graduate College of The University of Iowa, Dec. 2001.

* cited by examiner

*Primary Examiner*—Max F. Hindenburg
*Assistant Examiner*—Jonathan M Foreman
(74) *Attorney, Agent, or Firm*—Husch & Eppenberger LLC; H. Frederick Rusche (57) ABSTRACT

An improved support belt, support apparel, along with a process for creating such products. A mechanism by which support belts provide protection to the user is disclosed, which mechanism is generally applicable to all human joints.

13 Claims, 5 Drawing Sheets

SUPPORT APPAREL SUCH AS BACK SUPPORT AND SYSTEM

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention relates to support apparel such as back supports, wrist supports and the like, and to systems for designing and testing such apparel.

It is well known that the lifting of heavy objects can result in back injuries. Such injuries are even more likely to occur when the muscles supporting the back become fatigued, as can occur to truck drivers and the like as a result of the vibratory motion of the vehicle. In those circumstances, even the lifting of a light object can cause injury to the back. It should also be appreciated that other workers also require back support while performing their regular tasks. For example, fire fighters and construction workers, as well as laboratory workers, barbers and hairdressers, could use additional back support in performing their daily jobs. Many of these workers are required to (or choose to) wear certain items (hereinafter generically referred to as garments) which might interfere with the wearing of a support device such as a belt. For example, fire fighters, laboratory technicians, doctors, nurses, barbers and hairdressers often wear coats or jackets while performing their jobs. Likewise, construction workers conventionally wear tool belts, reflective vests, and the like. Conventional back supports are not always readily useable with these items of apparel.

Back supports have been provided to protect a person's back from injury. One such back support is sold by Chase Ergonomics under the trade designation Lumbar Lock. This back support includes a support belt which removably wraps around the lower abdomen or pelvis of a user and suspender-like shoulder straps which help prevent the support belt from sliding down during use. A pair of cinch straps are disposed over the support belt (which contains sewn in orthopedic boning stays) and are removably fastened together over the support belt. The support belt in combination with the cinch straps provide the desired back support. During non-active periods, wearers often loosen support tension or unclasp support belts completely, a practice generally encouraged by manufacturers of these devices. Many manufacturers of support belts simply recommend wearing support belts about the waist.

Various approaches have been taken in the past to improve upon support apparel such as back supports. For example, U.S. Pat. No. 5,548,843 to Chase et al. discloses an improved back support. That particular support discloses a back support with numerous adjustments including the use of a beaded pad (best shown in FIGS. 4 and 5) disposed at an adjustable position in the small of the back of the human wearer (see, e.g., pad 3 in FIG. 2).

It has been discovered, however, that the support of the '843 patent to Chase et al. can be improved. It appears that many back injuries, for example, are caused by the application of sudden, unexpected loads. The back apparently overcompensates for these loads and, in effect, injures itself. Back supports in general appear to reduce the possibility or severity of such injuries, but it has been discovered that they can be improved.

For example, the inventors of the present invention have discovered that currently available back supports are almost uniformly worn incorrectly—i.e. (at the user's waist or higher), a position that has been discovered to be less than optimal in reducing and eliminating injury. Moreover, it has been found that currently available back supports do not apply forces to the human torso in the optimal manner to reduce or eliminate back injuries.

More generally, presently available support apparel heretofore have been designed and tested using somewhat hit-or-miss methods. As a result, the efficacy of such apparel has varied, apparently inexplicably. It would be a major improvement to have a systematic method or system for designing such support apparel.

SUMMARY OF THE INVENTION

The various aspects of the present invention are directed to one or more of the following objects:

Accordingly, one object of the present invention is to provide an improved item of support apparel.

Another object is to provide a support which is worn in a way to improve its ability to reduce injury.

A third object is to provide a support with improved ability to protect the wearer against the effects of sudden and unexpected loads.

A fourth object is to provide an improved method of designing and testing support apparel.

A fifth object is the provision of an improved method for reducing back injury.

These and other objects will become apparent to those skilled in the art upon a review of the following description and accompanying drawings.

Briefly, in a first aspect of the present invention a method of reducing back injury includes the steps of placing a support belt about the lower trunk of a human user, tightening the support belt so as to apply pressure of at least a first level to predetermined points along the sides of the lower trunk, the support belt as a whole applying an average pressure that is lower than the first pressure around the lower trunk of the human user, the lower pressure being a second pressure level. The localized pressure of the first level (in combination with the more generalized pressure of the second level reduces the tendency of the muscles of the back of the human user to overcompensate to sudden or unexpected loading events. The pressure of the second level is comparable to that exerted by existing support belts, and may vary from user to user (depending upon how tight the cinch straps are tightened). The pressure of the second level is, in effect, the average pressure applied by the belt. Whatever the second level, the pressure of the first level is higher and applied to specific, localized positions (as described below) to achieve the advantageous results of the present invention.

In a second aspect of the present invention, a support belt for reducing back injury includes a support belt body sized to fit about the lower trunk of a human user, the support belt body having a front designed to be worn along the front of the lower trunk of the human user, a back designed to be worn along the back of the lower trunk of the human user, and sides designed to be worn along the sides of the human user. First and second sets of protrusions are disposed along the sides of the support belt body so as to press against the sides of the lower trunk of the human user during use. The protrusions of each set are of a size to apply pressure at recognizably separate points along each side of the lower trunk of the human user, so that the pressure applied by the protrusions reduces any tendency of the muscles of the back of the human user to overcompensate to sudden or unexpected loading events.

In a third aspect of the present invention, a method of reducing fatigue of a human includes the steps of instructing a human user to place a support belt about the lower trunk of a human user, in a position substantially lower than an average position for placement of support belts, placing the support belt in the substantially lower position, and tightening the support belt in the substantially lower position and retaining the support belt in the substantially lower position during the time the support belt is worn by the human user.

In a fourth aspect of the present invention, a method of improving lifting and lowering technique for a human includes the steps of instructing a human user to place a support belt about the lower trunk of the human user, in a position substantially lower than the average position for placement of support belts, placing the support belt in said substantially lower position, tightening the support belt in the substantially lower position and retaining the support belt in the substantially lower position during the time the support belt is worn by the human user.

In a fifth aspect of the present invention, a method of testing ergonomic support belts to evaluate the change in the estimated forces, moments, or stresses applied to an intervertebral disc upon applying a predetermined external load to a human subject includes the steps of fitting a plurality of human subjects with an ergonomic support belt, applying a predetermined load to the series of human subjects, measuring muscle response to the application of the predetermined external load of each human subject, estimating the forces, moments, or stresses applied to at least one intervertebral disc of the human subject, modifying the ergonomic support belt, and repeating these steps until a modified ergonomic support belt exhibiting minimized forces, moments, or stresses applied to at least one intervertebral disc is selected.

In a sixth aspect of the present invention, a method of reducing back injury in a human subject includes the steps of securing an ergonomic back support to the human such that a first force applying structure is disposed adjacent a first preselected location of the body of the human, and a second force applying structure is disposed adjacent a first preselected location of the body of the human, the first and second force applying structures in use applying substantially similar forces, moments, or stresses to the human body, said back support intermediate said first and second force applying structures applying forces, moments, or stresses to the human body that substantially differ from the forces, moments, or stresses applied by the first and second structures.

In a seventh aspect of the present invention, a system for modeling the response of a human subject to suddenly applied loads includes at least one sensor for measuring muscle response in the trunk of the human subject to the suddenly applied load, at least one sensor for measuring forces, moments or stresses at the feet of the human subject resulting from the application of the suddenly applied load, and a computer under software control for receiving input from the sensors for modeling the forces, moments, or stresses applied to at least one intervertebral disc of the human subject as a result of the suddenly applied load being applied to the human subject.

In an eighth aspect of the present invention a system for analyzing the response of human bodies to loading events such as unexpected or sudden loading events includes a link-dynamics model and a finite element model of the human body stored in a computer readable form, the model including models of bones, and further including models of soft tissues, including muscles and organs. The system further includes an apparatus for applying loading events to the bodies of human subjects, the loading events being selected from the group consisting of sudden, expected loading events and unexpected loading events. Sensors detect the response of each human body in at least one body location to the loading events. A computer receives data from the sensors and uses the models and the data from the sensors to determine the response of human subjects in at least a second location of the human body to the loading events.

In a ninth aspect of the present invention, an item of support apparel for reducing the risk of injury to a human user includes a support body for substantially encircling at least a part of a human body, at least one side panel disposed at a predetermined position along the support body, and a plurality of protrusions at the side panel to apply selectively increased pressure to the human body at a position determined by the location of the side panel.

BRIEF DESCRIPTION OF THE DRAWINGS

Similar reference characters indicate similar parts throughout the several views of the drawings.

DESCRIPTION OF THE INVENTION

Figure 1:
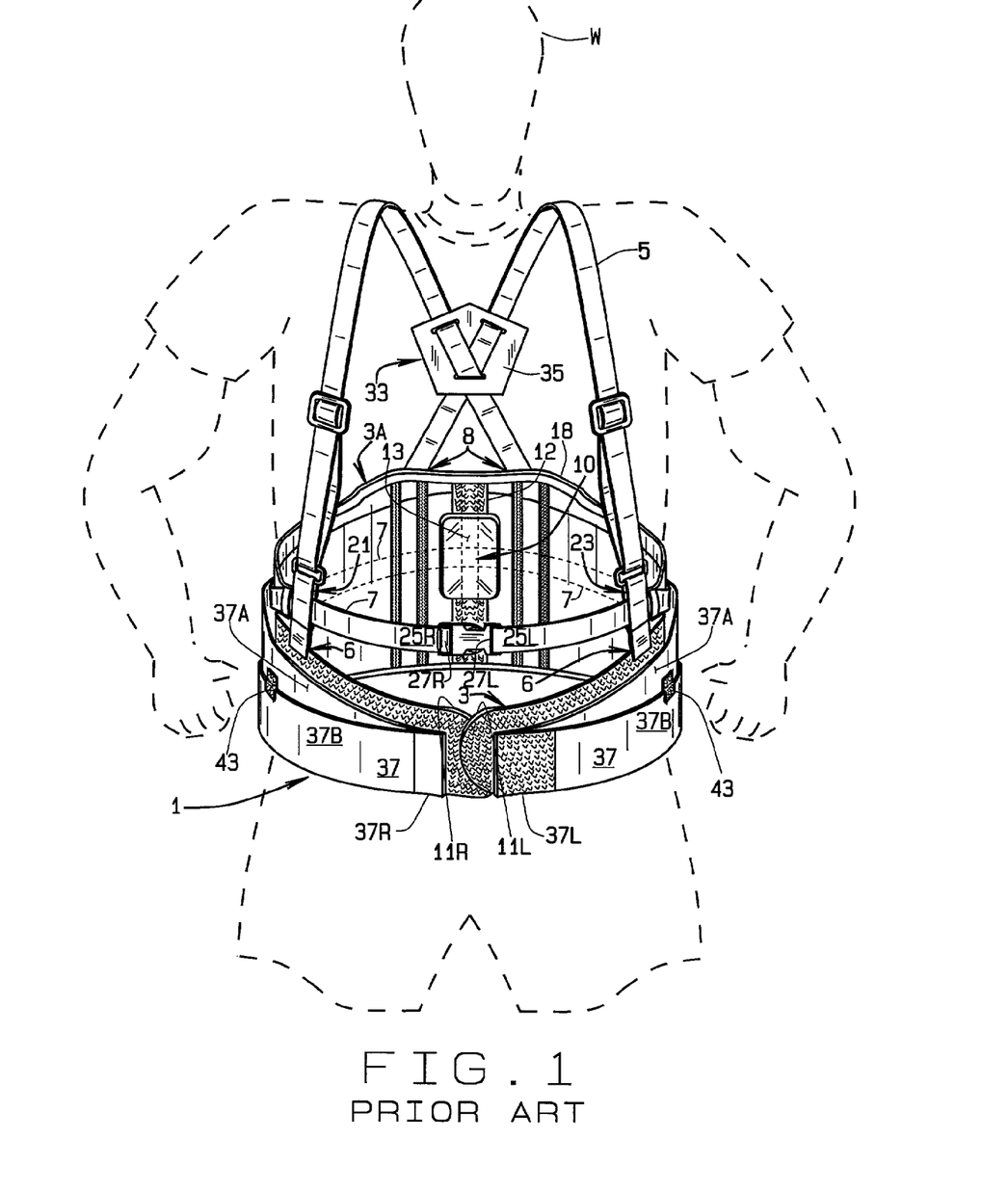
FIG. 1 is a perspective view of a prior art back support in a closed position, a wearer being shown in position.

Referring to FIG. 1, reference numeral 1 represents an illustrative embodiment of a prior art bank support. Back support 1 includes a support belt 3, shoulder strap or suspenders 5, and a secondary belt 7. It should be understood that belt 3 preferably includes support stays built therein in the conventional manner. Back support 1 is worn around the lower torso of a wearer "W" to provide support for the wearer's back. Shoulder straps 5 are connected to support belt 3 as shown at 6 on the left and right sides of the front portion of the best and arc connected to the back portion 3A of belt 3 as indicated at 8. The shoulder straps could include conventional quick-release fasteners if desired. The shoulder straps include a pair of loops 21 and 23 through which pass secondary belt 7.

Support belt 3 includes padded left and right free ends 11L and 11R. Both free ends have hook and pile fastener material secured to outer surfaces thereof. One of the free ends (free end 11L in FIG. 1) also has mating hook and pile fastener material secured to the inner surface thereof, which in combination with the corresponding fastener material of the other free end (free end 11R) is used by the wearer to removably secure belt 3 around the waist of the user. For a complete description of back support 1, see U.S. Pat. No. 5,548,843, the disclosure of which is incorporated herein by reference.

Figure 2:
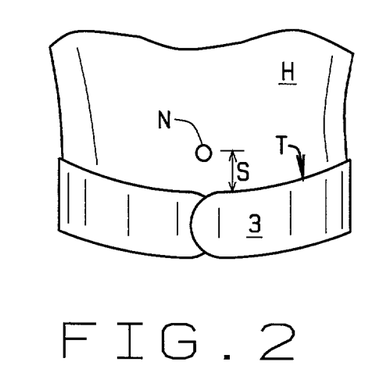
FIG. 2 is a perspective view, with parts broken away for clarity, illustrating improved placement of a support belt.

It has been discovered that the prior art support belt would be more effective if it were worn differently. Rather than being worn around the waist, support belts should be worn lower than shown in FIG. 1. Specifically, in accordance with the present invention, support belt 3 should be worn with the top, front edge T of the support belt 3 a distance "s" approximately one to approximately two inches below the navel N of the human user H, as shown in FIG. 2. When worn in this way, with the belt in a position substantially lower than the average placement of support belts, human fatigue of the wearer is reduced, as is the probability of back injury to the wearer. Wearing a support belt in this lower than normal position also results in reduced risk of injury during lifting and carrying of heavy objects. See, e.g., Udo et al., "The Effect of a Preventive Belt on the Incidence of Low Back Pain", Results presented in 1991 at Japan Industrial Hygiene Society Lumbago Study Group and Chungoku and Shikoku Districts Joint Industrial Hygiene Society.

Note that in FIG. 2, support belt 3 provides minimal (i.e., insignificant) support at or above the navel of the human user. If desired in the case of support belts, the belt of the present invention may also include placement structures such as interior belt loops, releasable shoulder straps, or back pad adjustments disposed to facilitate the placement of the support body at least one inch below the navel of a human user wearing the support apparel.

Figure 3:
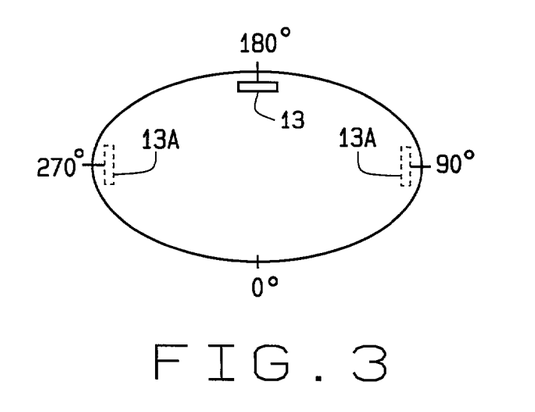
FIG. 3 is a schematic illustrating desired placement of force applying regions around the lower torso of a human user.

It has also been discovered that the prior art support belts can be improved in another way. As mentioned above, beaded pads such as those shown in FIGS. 4 and 5 of U.S. Pat. No. 5,548,843 are known for placement on support belts against the small of the back of the wearer. By way of illustration, a support belt 3 represented schematically as viewed from the top is shown in FIG. 3. In this representation, the front of the belt is at 0 degrees and the beaded pad 13 of the prior art is disposed at 180 degrees. It has been discovered that superior results (in terms of preventing back injury) are achieved when similar beaded pads are disposed at roughly at 90 degrees and 270 degrees instead of at 180 degrees, as indicated by phantom pads 13A in FIG. 3. More specifically, the center of the beaded pads are preferably located just slightly forward of the 90 and 270 degree positions on the belt. For simplicity of description, these positions are referred to herein as 90 and 270 degree, although variation (particularly toward the front of the belt) is contemplated. The additional pressure from pads 13A (or simply from beads or other protrusions incorporated into the belt, or some other mechanical expedient) reduces the tendency of the muscles of the back of the human user to overcompensate in response to sudden or unexpected loading events. It is believed they also supply active stimulation to the muscles, thereby reducing overcompensation as well as reducing fatigue of the user.

Although represented as beaded pads in FIG. 3, it should be understood that what is required is any structure for continuously applying force (and correspondingly, pressure) to the sides of the lower trunk of the human user in an amount greater than the average force (and pressure) applied by the support belt. A simple way to provide this additional force and pressure is with protrusions such as beads, but other mechanical means could be used. If beads or other protrusions are used, they need not be on a separate pad. Moreover, the protrusions are not intended to be limited to any particular distribution. Distributions with varying separations of varying numbers of protrusions of varying heights and shapes on varying sized regions in varying locations of the support all fall within the intended scope of the present invention.

Figure 4:
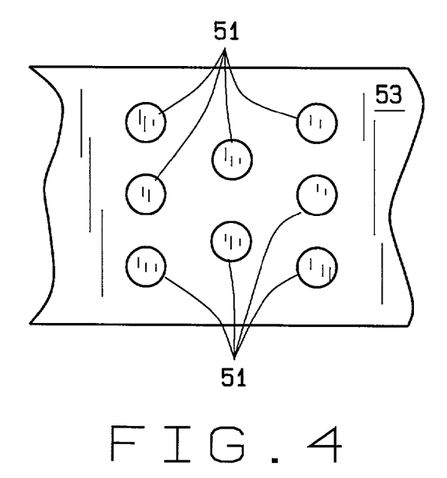
FIGS. 4 and 5 are front elevations of force applying areas of the support belt of the present invention.
Figure 5:
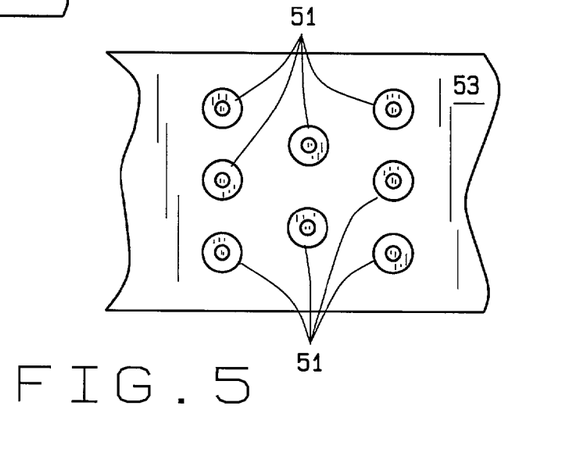

The protrusions, labeled 51, are shown in FIGS. 4 and 5 extending anteriorly (inwardly) from a side panel 53 of the support belt toward the body of the wearer. The protrusions of FIG. 4 are hemispherical, while those of FIG. 5 are conical. Other shapes could, of course be used. It is preferred that side panels 53 have a firmness that is higher than the average firmness of the support belt to provide a foundation for the protrusions. It should be understood that the location of each side panel (or the protrusions themselves, when no separate side panel is present) is determined from factors such as body shape, body size age, conditioning, and sex of the wearer.

The present invention does not exclude other pressure applying regions, but does contemplate additional application of force and pressure at either the 90 degree position or the 270 degree position, and preferably both. For example, in FIG. 3 it is preferred that additional pressure be applied at the 90 and 270 degree positions by beaded pads, integral protrusions, etc., either with or without the presence of beaded pad 13 at the intermediate 180 degree position.

The protrusions, labeled 51, are shown in FIGS. 4 and 5 extending anteriorly from a side panel 53 of the support belt 3 toward the body of the wearer. The protrusions of FIG. 4 are hemispherical, while those of FIG. 5 are conical. Other shapes could, of course be used. It is preferred that side panels 53 have a firmness that is higher than the average firmness of the support belt to provide a foundation for the protrusions. It should be understood that the location of each side panel (or the protrusions themselves, when no separate side panel is present) is determined from factors such as body shape, body size, age, conditioning, and sex.

Various placements and sizes of protrusions may be used. It has been found that good results are achieved when the protrusions of the two sets, at the 90 degree and 270 degree positions, are disposed between approximately four millimeters and approximately seventy millimeters, measured center to center, from each other. It has likewise been found that good results are achieved when the protrusions have a height of from approximately one eighth (3.175 millimeters) or one quarter inch (6.35 millimeters) to approximately one inch (25.4 mm). In the event that the protrusions are hemispherical, it is preferred that the protrusions have a corresponding radius. A variety of protrusion shapes may be used. Protrusions with circular cross-sections and hemispherical shapes are discussed above. But the protrusions could have cross-sections that are based on, but not limited to the following shapes: triangle, square, trapezoidal, rectangle, pentagon, hexagon, increasing numbers of sides approaching a circle, star-shaped with a variety of points and shapes of points, irregular, fractal, chaotic, spiral, variations on a buttressed or supported post, any of the above shapes with regions scalloped out in a regular or irregular or fractal fashion, rigid foam, honeycomb, etc. Similarly, the other views of the protrusion shape could indicate protrusion shapes based on, but not limited to: conical, pyramidal, triangular, rectangular, square, trapezoidal, ovoid, irregular, fractal, chaotic, tapered in various ways, a post with one or more buttresses or supports, etc. The region of the protrusion that contacts the user or the user's clothing could also have a variety of geometric characteristics including but not limited to: flat, continuous by some means of specification with the rest of the shape of the protrusion, inverted, recessed, pointed, undulating, dimpled, multiple recesses, multiple raised regions, fractal, chaotic, a surface with some specifiable roughness characteristic, bulbous, etc. The protrusions of each set apply pressure at recognizably separate points along each side of the lower trunk of the human user and the pressure applied by the protrusions reduces any tendency of the muscles of the back of the human user to overcompensate in response to sudden or unexpected loading events.

In those situations where the invention is being used in connection with joint braces other than back braces, the dimensions and distribution of those protrusions may be different than those set forth above. For example, the height of the protrusions for smaller joints could be as small as one sixteenth of an inch (1.6 millimeters). It should also be realized that the metric conversions of the English units given herein are not intended to limit the present invention to a particular degree of accuracy in the dimensions recited. The dimensions given are intended to be within plus/minus 10% or so.

It is preferred that the body of the support, and the side panels (if present) be composed of elastic material. Such material, such as Lycra [Spandex] is well-known. Such material typically has a warp axis and a weft axis transverse thereto. It is preferred, to properly apply pressure at the 90 and 270 degree positions, that the elastic material be cut so that the weft axis substantially encircles the human body (or the relevant joint in the cases of knee braces, wrist braces, etc.).

It would be desirable to be able to test in a meaningful way the effectiveness of support belts, both for measurement purposes and to aid in the design of improved belts. To that end, the present inventors have developed the system shown in FIGS. 6-8. This system, labeled 100, is particularly useful in modeling the response of a human subject to suddenly applied loads. The system shown includes sensors 101 (FIG. 7) for measuring muscle response of the subject, specifically erector muscle response in the subject's back and abdominal muscle response. Preferably these sensors 101 are surface mounted electrodes that measure EMG activity of the muscles at the L3 level, 3 cm bilaterally. The exact placement depends upon the particular analysis desired. The sensors on the abdominal muscles could be eliminated, with a corresponding loss of data. The system also includes a force plate 103 connected to a platform on which the subject stands to measure forces, moments, or stresses at the feet of the human subject resulting from the application of a suddenly applied load. A computer 105 (FIG. 7) under software control receives input from the sensors for modeling the forces, moments, or stresses applied to at least one intervertebral disc of the human subject as a result of the suddenly applied load being applied to the human subject. It is preferred that one or more motion sensors, such as Selspot IREDs 107 be used for measuring motion of at least one body segment (in this case leg and lower back motion) resulting from the application of the suddenly applied load. The motion was sensed at a suitable frequency, such as 100 Hz.

Figure 6:
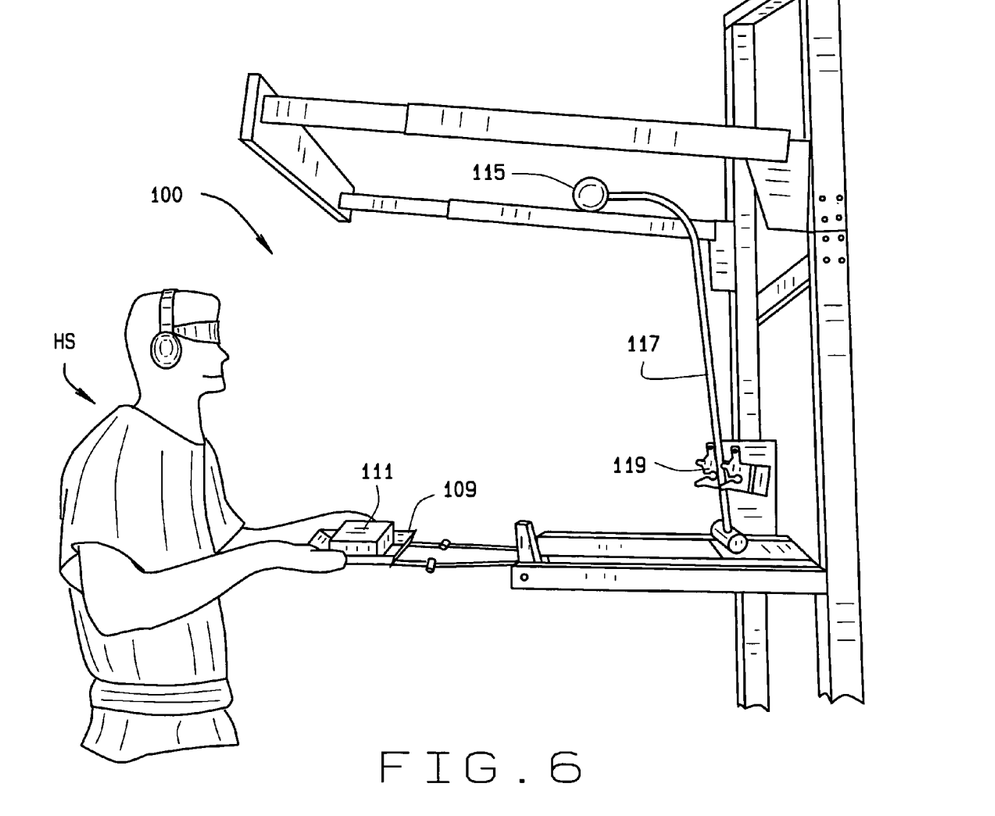
FIGS. 6 through 8 are schematic illustrations of a system for testing and improving support apparel.
Figure 7:
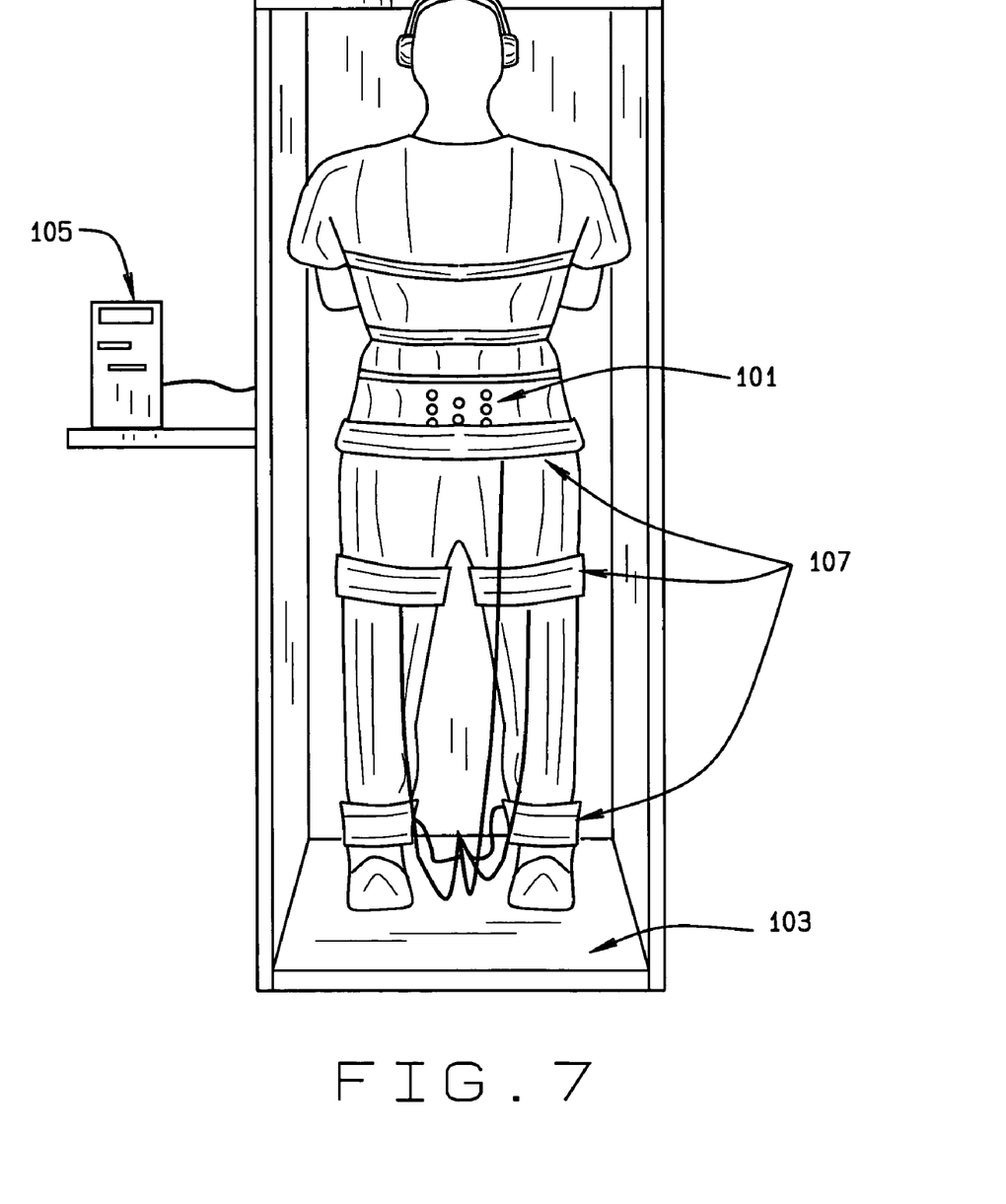

In FIG. 6, the human subject HS is shown blindfolded and wearing headphones (and listening to broadcast radio carrier noise) to eliminate various clues as to the timing of the application of the load. The subject holds a pan 109 containing a load cell 111 for measuring the time course of the magnitude of the suddenly applied load. Load cell 111, like all the sensors, is suitably connected to computer 105 in a conventional manner.

Figure 6A:
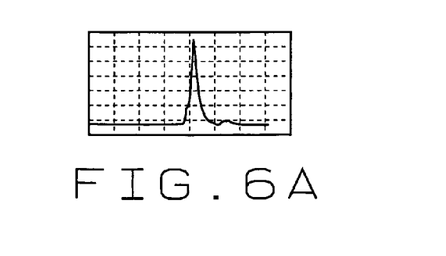
Figure 8:
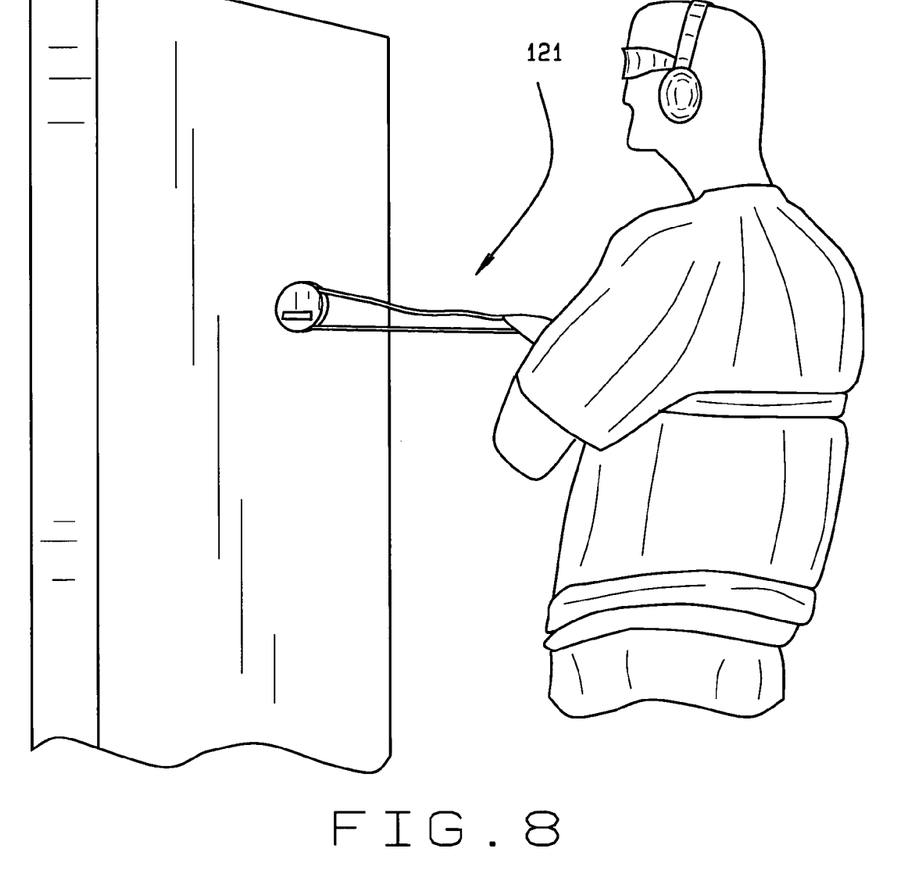
Figure 8A:
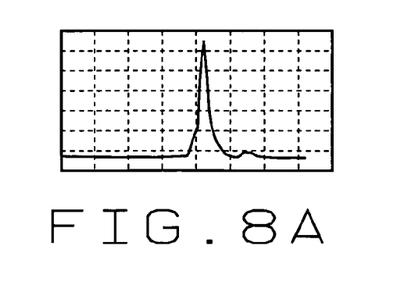

As shown in FIG. 6, the load of a predetermined amount (in this example 60 N) is applied by a ball 115 held by a releasable arm 117. The arm 117 is released from a latch 119 at a time unknown by the human subject, allowing the application of a sudden, unexpected load to the pan 109 being held by the subject. A typical load applied is shown in the chart in FIG. 6A. This load is transmitted through the arms of the subject to the subject's trunk. Similar loads may be applied directly to the chest of the subject by means of apparatus 121 (FIG. 8). Chest loads are also measured by a load cell, not shown. A typical chest load is shown in the chart in FIG. 8A.

The system 100 further includes a link-dynamics model and a finite element model of the human body stored in a computer readable form, which model includes models of bones, and further includes models of soft tissues, including muscles and organs. See, for example, the models found in the following papers, the disclosures of which are incorporated herein by reference: Lee, Seonghee (D G Wilder (supervisor), V K Goel, J B Park, J Rosecrance, M Kasra) Sudden load and the lower back: Effect of load application and lumbar support. Ph.D., Biomedical Engineering, The University of Iowa, Comprehensive exam: 12 Dec. 2000, Defense: 16 Jul. 2001; Kong, W. Z., Goel, V. K. and Gilbertson, L. G.: Prediction of Biomechanical Parameters in the Lumbar Spine during Static Sagittal Plane Lifting. ASME-J. Biomech. Engrg., 120, 273-280, 1998; Kong, W. Z., Goel, V. K., Gilbertson, L. G. and Weinstein, J. N.: Effects of Muscle Dysfunction on Lumbar Spine Mechanics—A Finite Element Study Based on a Two Motion Segments Model. Spine, 21, 2197-2207, 1996; and Goel, V. K., Kong, W. Z., Han, J. S., Weinstein, J. N. and Gilbertson, L. G.: A Combined Finite Element and Optimization Investigation of Lumbar Spine Mechanics with and without Muscles. Spine, 18, 1531-1541, 1993.

Computer 105 uses the models and the data from the sensors to determine the response of human subjects in a desired location, such as the response of muscle groups whose response is not being directly measured or the response of intervertebral disks, to the loading events.

The results from a single human subject are valuable, but the results of system 100 from a plurality of human subjects may be used more broadly, such as to predict human body responses to loading events, including predicting differences in human body responses as a function of body shape, body size, age, conditioning, and sex. The results from a plurality of subjects may also be used to predict long-term cumulative injuries, potential back injury, and potential joint injury. They may also be used to provide design information for support apparel such as back supports and joint braces.

In this latter case, a plurality of human subjects are fitted with an ergonomic support belt and the predetermined, unexpected load(s) is applied to each. For example, actual testing in this manner has been done using 24 right-handed male subjects. The system 100 estimates the forces, moments, or stresses applied to at least one intervertebral disc of the human subject. The testing is then repeated with different (i.e., modified) versions of the ergonomic support belt. This process is repeated as desired until one of the ergonomic support belts is selected that exhibits minimized forces, moments, or stresses applied to at least one intervertebral disc. This testing may reveal improved belt placement and improved belt structure, as described in the present application. It may also reveal other improvements heretofore undiscovered.

It should be understood that although the present invention is described in connection primarily with a back support, it is not limited in that way. The underlying discovery of how the body responds to surprise sudden loads may be used, as described above, for the development of other support apparel such as protective products for the ankle, knee, wrist, elbow and other joints, for example.

It is also believed that support belts of the type described above, with or without protrusions may be beneficial to other workers such as truck drivers, even while driving. People in seated, whole-body jolt/impact/vibration environments could benefit from these findings. In those cases, the forces, moments, or stresses could and would be applied to the body by means in addition to those through the chest or hands. Forces, moments, or stresses could also be applied in succession in time or simultaneously from many possible directions in that environment.

The forgoing description is set forth for illustrative purposes only. Numerous variations, within the scope of the claims, may be apparent to those skilled in the art. For example, snaps, rather than hook and pile fasteners may be used to close the belt 3 and to secure the cinch straps to the belt when the belt is being worn in its open position. Similarly, snaps, buckle fasteners, hook and eye fasteners, and the like may be used to hold the belt in its open position. These examples are merely illustrative.

What is claimed is:

1. A support belt for reducing back injury comprising:
    a support belt body sized to fit about the lower trunk of a human user, said support belt body having a front designed to be worn along the front of the lower trunk of the human user, a back designed to be worn along the back of the lower trunk of the human user, and sides designed to be worn along the sides of the human user, said support belt body being composed of elastic material;
    first and second sets of protrusions disposed along the sides of the support belt body so as to press against the sides of the lower trunk of the human user during use, at positions substantially 90° and 270° from the human user's navel;
    wherein the protrusions in a set are disposed between approximately four millimeters and approximately seventy millimeters, measured center to center, from each other, have a height of from approximately one-eighth inch (3.175 millimeters) to approximately one inch (25.4 mm), and have a hemispherical shape;
    said protrusions of each set being of a size to apply pressure at multiple recognizably separate points along each side of the lower trunk of the human user, whereby the pressure applied by the protrusions continually stimulates the user's muscles and thereby reduces any tendency of the muscles of the back of the human user to overcompensate in response to sudden or unexpected loading events.

2. An item of support apparel for reducing the risk of injury to a human user comprising:
    a support body for substantially encircling at least a part of a human body, said human body having a lower trunk;
    at least one side panel disposed at a predetermined position along the support body, said support body and side panel being composed of elastic material;
    a plurality of protrusions on the at least one side panel to apply selectively increased pressure to the human body at multiple recognizably separate points along a side of the lower trunk of the human body;
    wherein the item of support apparel is a support belt including placement structure for facilitating the placement of the support body at least one inch below the navel of a human wearing the support apparel.

3. The item of support apparel as set forth in claim 2 wherein the location of said at least one side panel is a function of at least one of body shape, body size, age, conditioning, and sex of the human wearer.

4. The item of support apparel as set forth in claim 2 wherein the item is a back support, and wherein no protrusions are disposed on the back support so as to contact the back of the human wearer's body when the back support is worn as intended.

5. The item of support apparel as set forth in claim 2 wherein the item of support apparel is a joint brace.

6. The item of support apparel as set forth in claim 2 wherein the elastic material has a warp axis and a weft axis transverse to the warp axis, the elastic material being cut so that the weft axis substantially encircles the body of the human wearer.

7. The item of support apparel as set forth in claim 2 wherein the placement structure is one selected from the group consisting of interior belt loops connected to the support body, adjustable shoulder straps with a release connected to the support body, and a back adjustment mechanism connected to the support body.

8. The item of support apparel as set forth in claim 2 wherein the support body at the side panel provides a foundation for the protrusions having a firmness higher than the average firmness of the support body.

9. The item of support apparel as set forth in claim 2 wherein the item is a back support, further including two side panels spaced along the support body to be disposed along the sides of a human user wearing the back support, each of the two side panels having a plurality of said protrusions disposed upon an interior surface thereof so as to contact the sides of the human wearer during normal use of the back support.

10. The item of support apparel as set forth in claim 9 wherein said protrusions on each of the two side panels are spaced between approximately 4 millimeters and 70 millimeters, measured center to center, from each other.

11. The item of support apparel as set forth in claim 10 wherein said protrusions have a height from approximately one quarter inch (6.35 mm) to approximately one inch (25.4 mm).

12. The item of support apparel as set forth in claim 10 wherein the protrusions have a uniform cross-sectional shape.

13. The item of support apparel as set forth in claim 12 wherein the protrusions have a hemispherical shape.

* * * * *